United States Patent [19]

MacCallum et al.

[11] Patent Number: 5,246,668

[45] Date of Patent: Sep. 21, 1993

[54] AIR SAMPLING AND ANALYSIS SYSTEM

[75] Inventors: Taber K. MacCallum, Oracle, Ariz.; Dennis R. Fitz, Claremont, Calif.

[73] Assignee: Space Biospheres Ventures, Oracle, Ariz.

[21] Appl. No.: 961,482

[22] Filed: Oct. 15, 1992

Related U.S. Application Data

[63] Continuation of Ser. No. 585,626, Sep. 20, 1990, abandoned.

[51] Int. Cl.$^5$ .......................................... G01N 31/12
[52] U.S. Cl. ..................................... 422/93; 422/62; 422/67; 422/83; 422/94; 436/55; 436/113; 436/181
[58] Field of Search ................. 422/62, 67, 83, 93, 422/94; 436/55, 113, 118, 122, 121, 158, 159, 181; 73/31.01, 31.02

[56] References Cited

U.S. PATENT DOCUMENTS

| | | | |
|---|---|---|---|
| 2,302,001 | 11/1942 | Schirm | 422/67 |
| 2,333,934 | 11/1943 | Jacobson | 436/181 |
| 2,821,462 | 1/1958 | McEvoy | 422/93 |
| 2,890,617 | 6/1959 | Lupfer et al. | 436/55 |
| 3,300,282 | 1/1967 | Risk et al. | 422/93 |
| 3,765,247 | 10/1973 | Riggs | 422/93 |
| 4,090,392 | 5/1978 | Smith et al. | 73/44.5 R |
| 4,432,939 | 2/1984 | Watanabe et al. | 436/113 |
| 4,601,211 | 7/1986 | Whistler | 73/863.33 |
| 4,705,669 | 11/1987 | Tsuji et al. | 422/93 |
| 4,722,830 | 2/1988 | Urie et al. | 422/62 |
| 4,891,186 | 1/1990 | Roberge et al. | 422/83 |

FOREIGN PATENT DOCUMENTS 40999 3/1980 Japan ................................. 436/113

OTHER PUBLICATIONS

Soviet Patent Abtracts S-X Electrical, week 8931, Jul. 5, 1989, Derwent Publications Ltd., London S03 *SU-1436-067 (Analyt Instr Res).*

Primary Examiner—Robert J. Warden
Assistant Examiner—Krisanne M. Thornton
Attorney, Agent, or Firm—Christie, Parker & Hale

[57] ABSTRACT

An air sampling and analysis system has a plurality of air sampling tubes extending between an analytical laboratory and a number of remote locations where samples are taken. Means are provided for continually drawing air through the sampling tubes during times when they are not connected to a analytical instrument for measuring concentration of various gases. Means are also provided adjacent to the inlet of at least some of the sampling tubes for converting a vapor which may not travel the full length of the sampling tube, to a gas which will travel the full length of the tube. The concentration of the vapor can be found by measuring the composition of the air sample with conversion and subtracting a similar composition without conversion. Examples of vapors that are converted include hydrogen sulfide and ammonia.

29 Claims, 1 Drawing Sheet

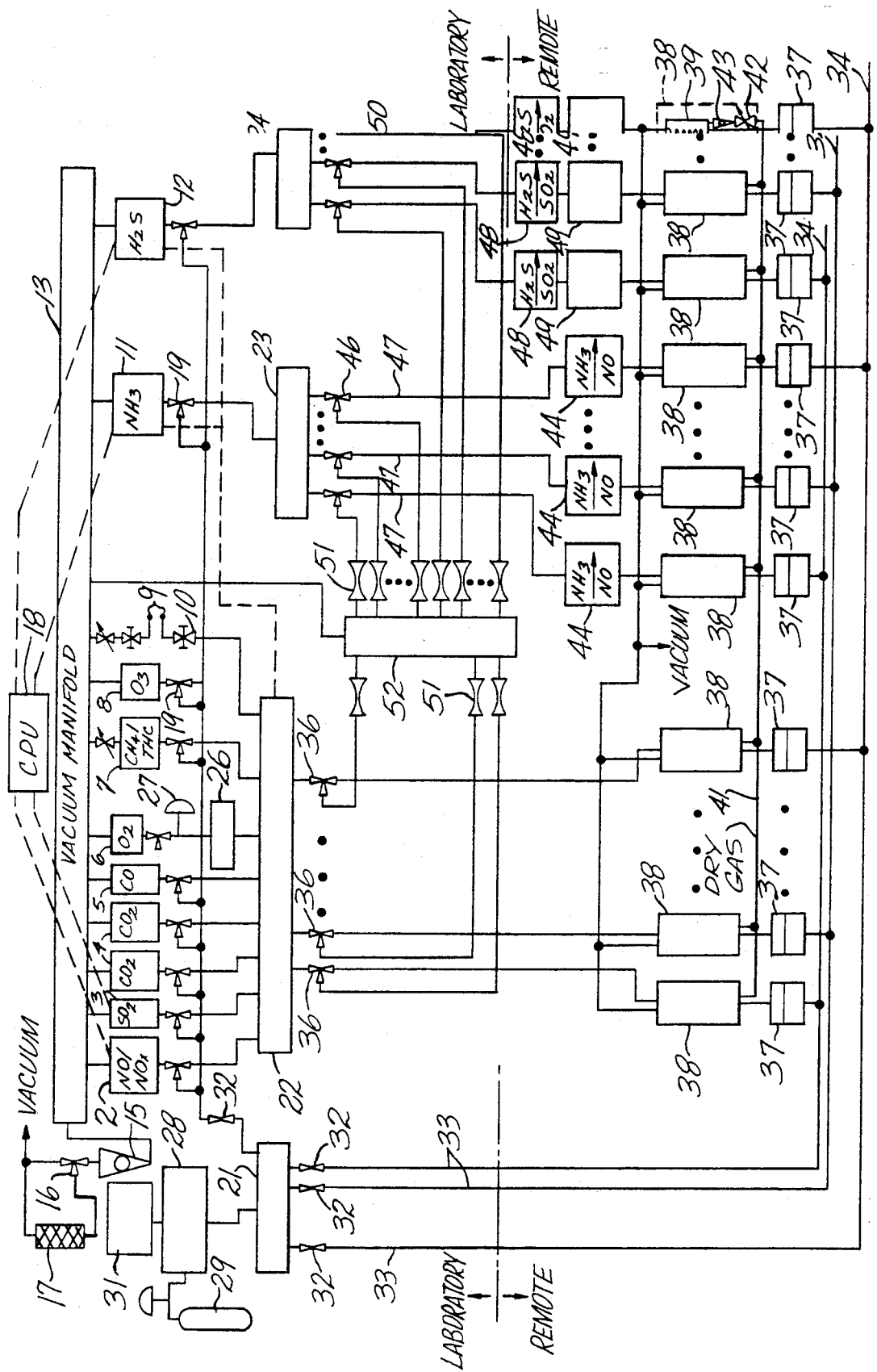

AIR SAMPLING AND ANALYSIS SYSTEM

CROSS-REFERENCE TO RELATED APPLICATION

This is a continuation of application Ser. No. 07/585,626, filed Sep. 20, 1990, now abandoned.

FIELD OF THE INVENTION

This invention relates to a system for sampling air at a plurality of remote locations and conveying the air to an analytical laboratory for analysis of the composition of the air.

BACKGROUND OF THE INVENTION

The earth itself comprises a biosphere in which microorganisms, plants, and animals, including humans, exist in a more or less steady state, wherein matter is a finite resource which is continually recycled. There is continual energy input in the form of solar radiation. The quantity of matter gained or lost to space outside the earth's atmosphere is minute. Thus, the earth is a closed ecological system which may be referred to herein as Biosphere I. Although the earth recycles matter continually between the soil, oceans, atmosphere, biomass, and the like, in a nearly steady state, there appears to be a drift of conditions as indicated by increasing carbon dioxide concentration in the atmosphere, the well-known "ozone hole," and other effects which may not have been detected as yet.

It is desirable to provide a microcosm of the biosphere known as earth for study of the interaction of components, and development of techniques for influencing our environment. Such experiments are difficult at best in the open system provided on earth, where matter is exchanged between the earth's environment and the experiment itself. It is, therefore, desirable to provide a system that is completely enclosed so that no matter is exchanged with the earth's environment. It is desirable to have humans within this miniaturized biosphere to provide control, and conduct scientific research within a closed system where conditions may be varied as desired.

Being a closed system having humans within the system requires that they be provided with a habitable atmosphere and a balanced diet for long-term health and that closed cycles be established for carbon, oxygen, nitrogen, other nutrients, water, and the like, so that the closed system may remain in a more or less steady state for the long periods of time required for conducting meaningful scientific research.

There is, therefore, being established near Oracle, Arizona, a completely closed ecological system referred to as Biosphere 2. The system completely encloses about one hectare of land and 175,000 cubic meters of space isolated from the earth's environment by an impermeable skin so that no matter is transferred. The above ground portion of the skin is largely transparent for receiving solar radiation. Electrical energy is provided to the closed system, and heat may be transferred to or from the system as required. Thus, the Biosphere 2 closed ecological system is closed as to matter, but open as to energy. For meaningful research, it also remains open for transfer of information.

The Biosphere 2 system provides facilities for occupation by eight humans who can remain sealed in the system under healthful living conditions for two years or more. Diverse plant, animal and microorganism populations in the system assure balancing of the ecology for long periods.

In Biosphere I, namely the earth, the interactions of and immense diversity of life species and chemical and physical reactions are such that a relatively steady state prevails without human intervention (if anything, humans tend to disrupt the steady state). In a smaller closed ecological system, however, it is improbable that a habitable environment would prevail for very long without human intervention.

For example, the atmosphere within the closed system could drift far from the composition usual in outside air, or could accumulate toxic vapors which could be harmful to the inhabitants. Thus, it is desirable to provide means for controlling the cycles of matter in the closed ecological system and to do that one needs to know what is happening in the atmosphere for detecting trends toward imbalance so that remedial steps may be taken before the undesirable condition becomes extreme. Furthermore, knowledge of the composition of the atmosphere is important data for evaluating experiments conducted within the closed system.

Biosphere 2 has a number of biomes within the closed system. There is, for example, a human habitat which serves as a residence and workplace for the people occupying the system. This is adjacent to an agricultural area which provides the principal food supply for the occupants. This is connected to a so-called wilderness area which has different ecological niches varying from a humid rain forest at one end to a desert at the other end. The organisms in these various areas within Biosphere 2 are continually exchanging various gases with the atmosphere within the closed system. Some plants may, for example, emit organic vapors as well as take up carbon dioxide and release oxygen during photosynthesis.

Since conditions may vary considerably from biome to biome, it is desirable to sample the air in various locations throughout Biosphere 2 for analysis. Trace quantities of some gases are of interest and precision instruments are therefore needed. To provided these costly instruments in each biome would b prohibitively expensive. Furthermore, to compare the analyses of gases between various biomes for subtle gradients, continual calibration of the various instruments would be required. For such reasons, it is desirable to employ precision instruments maintained in a single analytical laboratory. This introduces a requirement for gathering samples from remote locations and conveying them to the analytical laboratory. One could, of course, employ portable gas sampling bottles, but the required labor would be extraordinary for the regular monitoring that it desired. A remote sampling system is, therefore, desirable.

As with any sampling system it is important that the air sample delivered to the analysis instruments should be representative of the air at the remote location. It is desirable that the sampling system be arranged so that the taking of samples and analysis may be automated and controlled by computer inputs. It is also desirable that means be provided for calibrating the system to assure that the analytical data are truly representative of the air being sampled.

SUMMARY OF THE INVENTION

There is therefore provided in practice of this invention an air analysis system having a plurality of air sampling tubes with sample inlets at remote locations and extending to an analytical laboratory or the like. Means are provided for continually drawing air through each sampling tube so that the air in the tube is continually representative of the air to be sampled. Means are also provided for selectively disconnecting the means for drawing air from any selected sampling tube and connecting the selected sampling tube with one or more analysis instruments. Preferably dryers are provided at each remote location for drying air drawn into each sampling tube.

Furthermore, there are vapors which may not travel the full length of the sampling tube because of absorption or reaction. Therefore, means are provided adjacent to the inlet of the tube for converting the vapor to a gas which will travel the full length of the sampling tube. One may then determine the amount of the vapor by comparing the concentration of the gas with and without conversion. Examples of such conversion include converting ammonia to nitric oxide and converting hydrogen sulfide to sulfur dioxide.

BRIEF DESCRIPTION OF THE DRAWING

These and other features and advantages of the present invention will be appreciated as the same becomes better understood by reference to the following detailed description, when considered in connection with the accompanying drawing, which is a schematic block diagram of an air sampling and analysis system constructed according to principles of this invention.

DETAILED DESCRIPTION

The air sampling and analysis system can be considered as having two major parts. An analytical laboratory, illustrated in the upper portion of the schematic drawing, and a portion at a plurality of remote locations where samples are taken, illustrated in the lower portion of the drawing. Inert plastic or metal tubing (e.g., PTFE) connects the remote locations with the laboratory. The remote sampling locations may be many tens of meters or even hundreds of meters from the laboratory.

A variety of conventional commercially available gas analysis instruments may be used in the analytical laboratory. It is desirable to employ instruments which can operate automatically without manual manipulation so that analyses can be performed intermittently according to a prearranged schedule, day or night.

In an exemplary embodiment these instruments include an analyzer 2 for the concentration of nitrogen oxides, $NO_x$, and particularly, nitric oxide. Another instrument 3 is used for measuring the concentration of sulfur dioxide. In the illustrated embodiment, two instruments 4 are used in parallel for measuring carbon dioxide concentration. One of the carbon dioxide instruments has a low sensitivity range and the other has a high sensitivity range so that relatively broad swings in carbon dioxide concentration may be monitored. The $CO_2$ measuring instruments are connected to the vacuum manifold by pumps (not shown) for minimizing pressure variations at the instruments. Another instrument 5 is used for measuring the carbon monoxide concentration in the atmosphere.

An analytical instrument 6 suitable for measuring oxygen concentration in air is also used. Still another instrument 7 is used for measuring methane concentration and total hydrocarbons (THC) other than methane. Ozone is monitored with another instrument 8. Additional connection ports 9 are provided between toggle valves 10 so that other instruments may be connected into the system as may be desired for measuring other gases.

An analysis instrument 11 labeled in the drawing for measuring ammonia is actually similar to the instrument 2 for measuring nitric oxide. As explained in greater detail hereinafter, the ammonia concentration is found by converting ammonia to nitric oxide (NO) and finding the difference between the NO concentrations with and without such conversion. Similarly, the laboratory includes an instrument 12 for determining hydrogen sulfide concentration. This instrument is the same as the instrument 3 for measuring sulfur dioxide concentration. The concentration of hydrogen sulfide is determined after catalytically converting hydrogen sulfide to sulfur dioxide. Means are provided for scrubbing all the $SO_2$ from the gas stream before converting the $H_2S$ to $SO_2$.

Each of the analytical instruments is connecting to a vacuum manifold 13 maintained at a low pressure of about 50 centimeters of mercury. For monitoring purposes, the vacuum manifold is connected to the vacuum source by a rotameter 15. A three-way solenoid operated valve 16 permits bypassing of gas from the vacuum manifold through a scrubber 17 before going to the vacuum pumps. This may be used when toxic or noxious fumes are present in the system, such as may occur due to deliberate additions during calibration.

The inlet for each of the analytical instruments is connected to a three-way solenoid operated valve 19. The system includes a substantial number of three-way solenoid operated valves, only a portion of which are marked with identifying numerals in the drawing. The same symbol is used for each of these valves. The three-way valves 19 permit selective connection of each of the instruments to a calibration manifold 21 or a principal sample manifold 22. The ammonia-measuring instrument 11 may be selectively connected to a subsidiary sample manifold 23. The hydrogen sulfide analytical instrument 12 may be selectively connected to another subsidiary sample manifold 24. These instruments may also be connected to the main sample manifold 22 if desired as indicated by a dashed line in the drawing.

The oxygen analysis instrument 6 is connected to the sample manifold by a pump 26 controlled by a pressure regulator 27. Such a system is used since the preferred instrument for measuring the relatively high oxygen concentration determines an absolute quantity of oxygen and is therefore rather sensitive to pressure variations. The relatively minor effects of pressure variations on the other analytical instruments can be handled by calibration or calculation. The three-way valve for the oxygen analytical instrument 6 is not connected to the calibration manifold, but instead is connected to an oxygen source (not shown) for calibration.

Each of the analytical instruments is connected to the central processing unit 18 of a computer which provides control for the system and also gathers data, not only from the instruments in the laboratory, but from other portions of the environment being analyzed. Only a fraction of these connections are indicated in the drawing by dashed line. The computer also controls the many solenoid valves in the system. This permits automatic sampling and analysis on a scheduled basis at an arbitrary number of remote locations. The same computer may also be used for data analyses, correcting for interferences, and activating alarms in the event a gas being sampled exceeds a preset limit which indicates that some corrective action may be desired.

The calibration manifold 21 is connected to a calibrator 28 which provides controlled mixing of trace quantities of gas from a calibration gas source 29 with air from a pure air source 31. The calibration gas may be obtained from a gas generator or a container of stored gas of a desired composition. Solenoid valves 32 permit selective connection of the calibration manifold with the analytical instruments or to any of a plurality of calibration tubes 33 leading to the remote sampling locations.

The gas sampling system may be used for taking and analyzing samples of air from any arbitrary number of remote locations. For example, in Biosphere 2, an air sample may be taken at each of six different biomes within the closed system. Each of the remote sampling stations may be similar where it is anticipated that generally similar conditions will prevail at each station. Clearly one could, if desired, have different arrangements at various sampling stations.

Because of such similarities, common features are indicated schematically in the drawing or may be omitted from most of the sampling stations.

Typically, each sampling station inlet 34 is normally open to permit continual air flow. When one calibrates the system, corresponding valves 32 at the calibration manifold are opened and calibration gas passed through the tubes 33. The quantity of gas introduced for calibration is greater than the amount drawn through the sample tubes for analyses. The excess gas is discharged through the open end of the sampling station inlet, thereby excluding air from the biome from entering the tube during calibration.

The sampling station inlets may also be used for temporarily connecting a permeation tube calibrator or the like (not shown), at a sampling location for calibration of the system, particularly for vapors such as ammonia or hydrogen sulfide which may not travel the full length of the calibration tubes 33 from the calibration manifold.

One may also temporarily introduce nitrogen into the sampling station inlets for a sufficient time to be lethal to aerobic organisms that might populate the tubing and interfere with accurate analyses. This may be done by going to the inlet with a portable nitrogen supply, or may be done by introducing nitrogen via the calibration tubing 33 at a flow rate greater than drawn through the sample tubes.

Each of the sampling stations in this embodiment has three taps to which air samples are routed. A principal connection for each sample inlet is to the main sample manifold 22 which provides connections to the analytical instruments in the laboratory. Each of these connections to the main sample manifold is made by way of a three-way solenoid valve 36. These valves may be selectively opened so that each sample inlet is, in turn, connected to the main sample manifold for analysis of air drawn into the system through that respective sample inlet.

Each tap at the sample inlets has a filter 37 and dryer 38. The filter is simply to keep debris out of the sampling tubes. Each dryer comprises a conventional diffusion drying tube 39. Such a diffusion drying tube comprises a chamber containing a membrane permeable to water vapor. A dry vacuum is drawn on one side of the membrane and water vapor from the other side diffuses through the membrane for drying the gas sample. The vacuum side of each diffusion drying tube is connected to a source of dry compressed air 41 by way of a manual flow control valve 42 and rotameter 43 for controlling dry air flow through the vacuum side of the diffusion tube dryer.

The filter 37 is connected on the other side of the membrane so that the gas samples are dried at the sample locations and little, if any, water vapor travels through the sampling tubes. Diffusion tube dryers are desirable since they operate without periodic recharging or other maintenance. If desired, intermittent measurements of relative humidity may be made of the air continually drawn through each sampling station inlet to verify that the dryers are operating properly.

Another group of sample taps, one for each sample inlet, are connected to catalytic converters 44 which convert ammonia in the air to nitric oxide. Each of these catalytic converters is connected to one of the subsidiary sample manifolds 23 by a three-way solenoid valve 46. The catalytic converters are located adjacent to each sample inlet, upstream from long sampling tubes 47 leading to the subsidiary sample manifold. Ammonia in the air samples may react or absorb unpredictably in the long sampling tubes. Such unpredictability is avoided by converting the ammonia to nitric oxide which will travel the full length of the sampling tubes for analysis in the analytical laboratory.

Similarly, another set of sample taps, one for each sample inlet, is connected to scrubbers 49 for removing sulfur dioxide from the gas stream and catalytic converters 48 which convert hydrogen sulfide to sulfur dioxide. These converters are provided adjacent to each sample inlet since hydrogen sulfide is also a vapor that may travel unpredictably through long sampling tubes 50 leading to the other subsidiary sample manifold 24. The converted sulfur dioxide will travel through the full length of the sampling tubes. Hydrogen sulfide is then determined directly by the analytical instrument 12.

Ammonia concentration is not measured directly, it is measured indirectly by subtraction. Each of the NO/-$NO_x$ and $NH_3$ measuring instruments 2 and 11 are the same. Both are set up for alternately measuring two gas samples in rapid succession. The gas actually measured in each instrument is NO. In the NO/$NO_x$ instrument one gas sample is the gas stream directly from the sample inlet. The NO concentration in this sample is measured directly. The other sample is from the same stream, but is passed through a catalytic converter (not shown) which is part of the instrument and which converts all $NO_x$ compounds to NO. The measurements of NO in the two samples are then subtracted to yield a value for the $NO_x$ in the sample.

The amount of ammonia is determined in a generally similar manner. In the $NH_3$ instrument 11, however, one sample passes through a catalytic converter which converts all $NO_x$ compounds to NO. The other sample passes through a catalytic converter which converts ammonia and all the $NO_x$ compounds to NO. The difference between these two readings is the ammonia concentration in the air sample.

It is desirable to use a single instrument for these measurements since instrument drift and calibration are not critical to the accuracy of the measurements. In fact, it is desirable to make all the measurements with individual instruments in an analytical laboratory instead of a plurality of instruments at each location in the closed system.

One of the subjects of interest is rather small gradients of gas concentration between different parts of the system. Separate instruments at various locations would require precise calibration for making the subtractions needed to identify such gradients. A tubing system between the instruments and the remote locations permits such comparisons to be made accurately. The differences can actually be determined with greater precision than the absolute accuracy of the measuring instrument would indicate. This desideratum is not unique to measurement of gas concentrations in the closed ecological system. It is also desirable in a system for measuring spread of noxious gas from a leak or spill, for example, where gradients in concentration indicate the nature of the plume.

Each of the sampling tubes is connected to a sample manifold 22, 23 or 24 by a three-way solenoid valve. The third valve connection for each of these valves is to a small capillary orifice 51. Each of the capillary orifices is, in turn, connected to a vacuum manifold 52. The three-way valves are normally in a position that causes air to be drawn into each sample inlet through the respective sampling tubes to the capillary orifice. The orifice serves to restrict flow to a low rate, but maintains flow through all the sampling tubes for continual purging, and assurance that the air in the sampling tubes has a composition representative of the air at the sample inlet.

The solenoid valves permit disconnecting the sampling tube from the vacuum manifold and connecting it to the respective sample manifold when it is desired to analyze the gas from a particular sample inlet. The analysis may be made promptly upon making such a connection because of the continual drawing of air through the sampling tubes or may be delayed a sufficient time for air to travel from the remote sampling inlet to the analytical laboratory. Prompt measurements can be made since the drift of gas composition is quite slow by comparison with the sampling intervals involved.

Although one embodiment of gas sampling and analysis system and minor variations have been described in detail herein, it will be readily apparent that many modifications can be made. For example, the system is described in the context of air sampling in a closed ecological system. A similar system could be used in many other settings. For example, an array of remote locations may be provided around a chemical plant for monitoring air quality and detecting leaks, and for tracking a plume of leaking chemical if that should occur. The analytical instruments in such an embodiment would be selected for their sensitivity to particular chemicals likely to be present in the vicinity. A large array of remote locations may be maintained on standby for observation of accidental leakage or spills.

In the embodiment of air sampling and analysis system hereinabove described and illustrated, calibration tubes 33 run from the calibration manifold to the remote sampling locations so that calibrations may be made through the sampling tubes. If desired, alternative connections can be made so that the calibration tubes double as sampling tubes. The particular gas analysis instruments described are appropriate for the tests to be run in this one situation. Other instruments would be useful for monitoring other gases or vapors. Many other modifications and variations will be apparent to those skilled in the art and it is therefore to be understood that within the scope of the appended claims, the invention may be practiced otherwise than as specifically described.

What is claimed is:

1. An air analysis system comprising:
   a plurality of air sampling tubes having sampling inlet ends at remote locations;
   at least one air analysis instrument for analyzing a sample of air for traces of environmental gases;
   means for continually drawing air through each sampling tube from the remote location to the vicinity of the air analysis instrument;
   means associated with the sampling tubes and the analysis instrument for selectively disconnecting the means for drawing air from any selected sampling tube and connecting the selected sampling tube with the analysis instrument;
   means at the remote locations connected to the inlet end of each of at lest a portion of such sampling tubes for converting an environmental gas present in trace quantities which will not pass unchanged through the sampling tube to the analysis instrument to a second gas which will pass unchanged through the sampling tube to the analysis instrument;
   wherein the air analysis instrument comprises means for analyzing an air sample drawn through such a sample tube for traces of the second gas; and
   means in association with the analysis instrument for determining the concentration of the environmental gas as a function of the concentration of the second gas.

2. An air analysis system as recited in claim 1 wherein the means for drawing air comprises a vacuum manifold and a flow control orifice connecting each sampling tube and the vacuum manifold.

3. An air analysis system as recited in claim 1 further comprising means connected to the inlet of a sampling tube at each remote location for drying air drawn into the sampling tube.

4. An air analysis system as recited in claim 3 wherein the means for drying air drawn into the sampling tube comprises a membrane permeable to water vapor having one face exposed to the air drawn into the sample tube and means for partially evacuating the other face of the membrane for diffusion of water vapor from the air drawn into the sample tube to the evacuated face.

5. An air analysis system as recited in claim 1 wherein the means connected to the inlet of a sapling tube at each remote location comprises means for converting ammonia to nitrogen oxide in air drawn into the sampling tube.

6. An air analysis system as recited in claim 1 wherein the means connected to the inlet of a sampling tube at each remote location comprises means for converting hydrogen sulfide to sulfur dioxide in air drawn into the sampling tube.

7. An air analysis system as recited in claim 6 further comprising means for scrubbing sulfur dioxide from air drawn into the sampling tube before the means for converting hydrogen sulfide to sulfur dioxide.

8. An air analysis system as recited in claim 1 further comprising means for introducing a gas lethal to aerobic organisms into the inlet of each sampling tube at a remote location.

9. An air analysis system comprising:
   a plurality of air sampling tubes having sampling inlet ends at remote locations;
   at least one air analysis instrument;

means for continually drawing air through each sampling tube from the remote location to the vicinity of the air analysis instrument;

means associated with the sampling tubes and the analysis instrument for selectively disconnecting the means for drawing air from any selected sampling tube and connecting the selected sampling tube with the analysis instrument;

means at the remote locations connected to the inlet end of each of at lest a portion of such sampling tubes for converting an environmental gas present in trace quantities which will not pass unchanged through the sampling tube to the analysis instrument to a second gas which will pass unchanged through the sampling tube to the analysis instrument; and means for introducing a calibration gas into the inlet of each sampling tube at a remote location for calibrating the air analysis system.

10. An air analysis system comprising:

a plurality of air sampling tubes having sampling inlet ends at remote locations;

at least one air analysis instrument;

means associated with the sampling tubes and the analysis instrument for selectively connecting a selected sampling tube with the analysis instrument;

means at the remote locations connected to the inlet end of each of at least a portion of such sampling tubes for converting an environmental gas present in trace quantities which will not pass unchanged through the sampling tube to the analysis instrument to a second gas which will pass unchanged through the sampling tube to the analysis instrument;

means for continually purging each sampling tube when not connected to an analysis instrument; and means for introducing a calibration gas into the inlet of each sampling tube at a remote location for calibrating the air analysis system.

11. An air analysis system as recited in claim 10 further comprising means for drying air drawn into the sampling tube connected to the inlet of each sampling tube at each remote location.

12. An air analysis system comprising:

a plurality of air sampling tubes having sampling inlet ends at remote locations;

at least one air analysis instrument;

means associated with the sampling tubes and the analysis instrument for selectively connecting a selected sampling tube with the analysis instrument;

means for converting ammonia to nitrogen oxide in air drawn into the sampling tube connected to a sampling tube at each remote location;

means for continually purging each sampling tube when not connected to an analysis instrument; and means for introducing a calibration gas into the inlet of each sampling tube at a remote location for calibrating the air analysis system.

13. An air analysis system comprising:

a plurality of air sampling tubes having sampling inlet ends at remote locations;

at least one air analysis instrument;

means associated with the sampling tubes and the analysis instrument for selectively connecting a selected sampling tube with the analysis instrument;

means for converting hydrogen sulfide to sulfur dioxide in air drawn into the sampling tube connected to a sampling tube at each remote location;

means for continually purging each sampling tube when not connected to an analysis instrument; and means for introducing a calibration gas into the inlet of each sampling tube at a remote location for calibrating the air analysis system.

14. An air analysis system comprising:

a plurality of air sampling tubes having sampling inlet ends at remote locations;

at least one air analysis instrument;

means associated with the sampling tubes and the analysis instrument for selectively connecting any specific sampling tube with at least one selected analysis instrument;

means at the remote locations connected to the inlet end of each of at least a portion of such sampling tubes for converting an environmental gas present in trace quantities which will not pass unchanged through the sampling tube to the analysis instrument to a second gas which will pass unchanged through the sampling tube to the analysis instrument;

a calibration manifold;

means for introducing a calibration gas into the calibration manifold; and means for connecting the calibration manifold to the inlet end of each of the air sampling tubes adjacent to the remote location.

15. An air analysis system as recited in claim 14 wherein the means for connecting sampling tubes to selected analysis instruments comprises:

a sample manifold;

means for selectively connecting each sampling tube to the sample manifold; and means for selectively connecting each analysis instrument with the sample manifold.

16. An air analysis system as recited in claim 15 wherein each means for selectively connecting a sampling tube and the sample manifold comprises a three way valve for alternatively connecting a sampling tube with a means for drawing air through the tube or with the sample manifold.

17. An air analysis system as recited in claim 15 comprising means for drawing air through each sampling tube and a three way valve connected between each sampling tube and the means for drawing air through the tube and the sample manifold.

18. An air analysis system as recited in claim 14 comprising means for connecting a selected sampling tube with a plurality of gas analysis instruments.

19. An air analysis system comprising:

at least one sample collection tube for collecting air samples at a remote location;

an air dryer connected to the inlet of the sample collection tube at the remote location for drying sampled air;

catalytic means connected to the inlet of the sample collection tube for converting hydrogen sulfide in sampled air to $SO_2$ at the remote location;

means for measuring a first concentration of $SO_2$ in sampled air from the catalytic means;

means for measuring a second concentration of $SO_2$ in sampled air without conversion of hydrogen sulfide; and means for determining concentration of hydrogen sulfide in sampled air as a difference between the first and second measurements.

20. A method for analyzing air for vapors at remote locations comprising the steps of:
drawing air into a sampling tube;
adjacent to the inlet end of the tube, converting a vapor which may not travel the full length of the sampling tube to a gas which will travel the full length of the sampling tube;
conveying air containing the converted gas through the tube to an analysis instrument for analyzing air for chemical composition;
analyzing air containing the converted gas for the concentration of the converted gas; and
determining to concentration of the vapor before conversion as a function of the concentration of the converted gas.

21. A method as recited in claim 20 wherein the vapor comprises hydrogen sulfide and the converting step comprises converting the hydrogen sulfide to sulfur dioxide.

22. A method as recited in claim 21 comprising the step of removing sulfur dioxide from the air before converting hydrogen sulfide.

23. A method as recited in claim 20 wherein the vapor comprises ammonia and the converting step comprises converting the ammonia to nitrogen oxide.

24. A method as recited in claim 20 further comprising the steps of:
analyzing a second sample of air to determine a second concentration of the gas without conversion at the inlet to the sampling tube; and
determining the original concentration of the vapor at the inlet to the sampling tube by subtracting the second concentration from the concentration of the gas in the first analysis for determining the original concentration of the vapor at the inlet to the sampling tube.

25. A method for analyzing air at a plurality of remote locations comprising the steps of:
continually drawing air into an inlet to each of a plurality of sampling tubes at remote locations to a location adjacent to an analytical facility;
intermittently withdrawing air from each of the sampling tubes to a gas analysis instrument at the analytical facility;
analyzing at least a portion of the chemical composition of the withdrawn air; and
converting vapors which may not travel the full length of a sampling tube to a gas which will travel the full length of the sampling tube adjacent to the inlet of at least a portion of the sampling tubes; and
measuring the concentration of the converted gas in an air sample.

26. A method as recited in claim 25 comprising the steps of:
analyzing the air containing the converted gas for a first concentration of the converted gas;
analyzing air for a second concentration of the same gas without conversion at the inlet to the sampling tube; and
determining the original concentration of the vapor at the inlet to the sampling tube by subtracting the second concentration from the first concentration for determining the original concentration of the vapor at the inlet to the sampling tube.

27. A method for analyzing air at a plurality of remote locations comprising the steps of:
continually drawing air into each of a plurality of sampling tubes having inlets at remote locations to a location adjacent to an analytical facility;
intermittently withdrawing air from each of the sampling tubes to a gas analysis instrument at the analytical facility;
analyzing the composition of the withdrawn air; and
intermittently introducing a gas lethal to aerobic organisms into the inlet of each sampling tube at a remote location.

28. A method for analyzing air at a plurality of remote locations comprising the steps of:
continually drawing air into an inlet to each of a plurality of sampling tubes at remote locations and conveying the air to a location adjacent to an analytical facility;
adjacent to the inlet end of the tube, converting a vapor which may not travel the full length of the sampling tube to a gas which will travel the full length of the sampling tube;
intermittently withdrawing air from each of the sampling tubes to a gas analysis instrument at the analytical facility;
analyzing the composition of the withdrawn air; and
intermittently introducing a calibration gas into the inlet of each sampling tube at a remote location for calibrating the sampling tubes as well as the analysis instrument.

29. A method as recited in claim 28 wherein the calibration gas is introduced into the sampling tube by way of a tube from the analytical facility.

* * * * *

UNITED STATES PATENT AND TRADEMARK OFFICE
CERTIFICATE OF CORRECTION

PATENT NO. : 5,246,668
DATED : September 21, 1993
INVENTOR(S) : Taber K. MacCallum; Dennis R. Fitz It is certified that error appears in the above-indentified patent and that said Letters Patent is hereby corrected as shown below:

Column 10, line 12, delete "at least one air analysis instrument" and insert therefor
-- a plurality of gas analysis instruments --.

Signed and Sealed this

Thirty-first Day of May, 1994

*Attest:*

BRUCE LEHMAN

*Attesting Officer*    *Commissioner of Patents and Trademarks*